(12) United States Patent
Barrows et al.

(10) Patent No.: US 10,039,447 B2
(45) Date of Patent: Aug. 7, 2018

(54) MOLDED ELECTRONIC STRUCTURES IN BODY-MOUNTABLE DEVICES

(71) Applicant: Verily Life Sciences LLC, Mountain View, CA (US)

(72) Inventors: Daniel Patrick Barrows, Sunnyvale, CA (US); Zenghe Liu, Alameda, CA (US); Jeffrey George Linherdt, Pleasanton, CA (US); James Etzkorn, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 899 days.

(21) Appl. No.: 14/139,865

(22) Filed: Dec. 23, 2013

(65) Prior Publication Data

US 2015/0173602 A1    Jun. 25, 2015

(51) Int. Cl.
*A61B 5/05* (2006.01)
*A61B 3/10* (2006.01)
(Continued)

(52) U.S. Cl.
CPC ............ *A61B 3/101* (2013.01); *A61B 5/1477* (2013.01); *A61B 5/1486* (2013.01); *A61B 5/14507* (2013.01); *A61B 5/6821* (2013.01); *G02C 7/04* (2013.01); *A61B 5/002* (2013.01); *A61B 5/14532* (2013.01); *A61B 2560/0214* (2013.01); *A61B 2562/12* (2013.01)

(58) Field of Classification Search
CPC ......... A61B 3/10; A61B 5/1477; A61B 3/101; A61B 5/14507; A61B 5/1486; A61B 5/6821; A61B 5/002; A61B 2562/12; A61B 2560/0214; A61B 5/14532; G02C 7/04

See application file for complete search history.

(56) References Cited

U.S. PATENT DOCUMENTS

| 4,126,138 A * | 11/1978 | Isen ..................... G02C 7/04 351/159.02 |
| 6,579,918 B1 * | 6/2003 | Auten ................... A61F 2/145 351/159.33 |

(Continued)

FOREIGN PATENT DOCUMENTS

| EP | 2631704 A1 | 8/2013 |
| WO | 2012013353 A1 | 2/2012 |

OTHER PUBLICATIONS

International Search Report and Written Opinion of International Application No. PCT/US2014/071986 dated Apr. 24, 2015.

*Primary Examiner* — Jacqueline Cheng
*Assistant Examiner* — Eric Messersmith
(74) *Attorney, Agent, or Firm* — McDonnell Boehnen Hulbert & Berghoff LLP

(57) ABSTRACT

Molded electronic structures configured for use in body-mountable devices and methods for embedding molded electronic structures in a body-mountable device are described. An example method may include molding an electronic structure to have first curvature corresponding to a first radius of curvature. The electronic structure may include an antenna, a sensor, and an electronic device. The example method may also include adhering the molded electronic structure to a first polymer layer. The example method may additionally include forming a second polymer layer over the molded electronic structure adhered to the first polymer layer.

16 Claims, 9 Drawing Sheets

(51) Int. Cl.
*A61B 5/1477* (2006.01)
*A61B 5/145* (2006.01)
*A61B 5/1486* (2006.01)
*G02C 7/04* (2006.01)
*A61B 5/00* (2006.01)

(56) References Cited

U.S. PATENT DOCUMENTS

| | | |
|---|---|---|
| 8,096,554 B1 | 1/2012 | Amirparviz et al. |
| 2010/0103368 A1 | 4/2010 | Amirparviz et al. |
| 2012/0177576 A1 | 7/2012 | Hu et al. |
| 2012/0236524 A1 | 9/2012 | Pugh et al. |
| 2012/0245444 A1 | 9/2012 | Otis et al. |
| 2012/0257188 A1* | 10/2012 | Yan ................... G01N 33/49 356/40 |
| 2013/0135578 A1 | 5/2013 | Pugh et al. |
| 2013/0194540 A1* | 8/2013 | Pugh .................. A61F 2/1635 351/159.03 |
| 2013/0281774 A1 | 10/2013 | Honaryar et al. |
| 2014/0211149 A1* | 7/2014 | Hansen ............ B29D 11/00048 351/159.33 |

* cited by examiner

US 10,039,447 B2

MOLDED ELECTRONIC STRUCTURES IN BODY-MOUNTABLE DEVICES

BACKGROUND

Unless otherwise indicated herein, the materials described in this section are not prior art to the claims in this application and are not admitted to be prior art by inclusion in this section.

A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose) in a tear film of a user wearing the eye-mountable device. The body-mountable device may also be configured to monitor various other types of health-related information.

SUMMARY

In one aspect, a method involves molding an electronic structure to have a first curvature corresponding to a first radius of curvature. The electronic structure may include an antenna, a sensor, and an electronic device. The method may also involve adhering the molded electronic structure to a first polymer layer. Additionally, the method may involve forming a second polymer layer over the molded electronic structure adhered to the first polymer layer.

In another aspect, a device includes a first polymer layer. The device also includes a molded electronic structure that has a first curvature corresponding to a first radius of curvature. The molded electronic structure is adhered to the first polymer layer. Further, the molded electronic structure comprises an antenna, a sensor, and an electronic device. The device may additionally include a second polymer layer that is formed over the molded electronic structure adhered to the first polymer layer.

In yet another aspect, a system is disclosed. The system includes means for molding an electronic structure to have a first curvature corresponding to a first radius of curvature. The electronic structure may include an antenna, a sensor, and an electronic device. The system also includes means for adhering the molded electronic structure to a first polymer layer. The system further includes means for forming a second polymer layer over the molded electronic structure adhered to the first polymer layer.

These as well as other aspects, advantages, and alternatives, will become apparent to those of ordinary skill in the art by reading the following detailed description, with reference where appropriate to the accompanying drawings.

DETAILED DESCRIPTION

Figure 1:
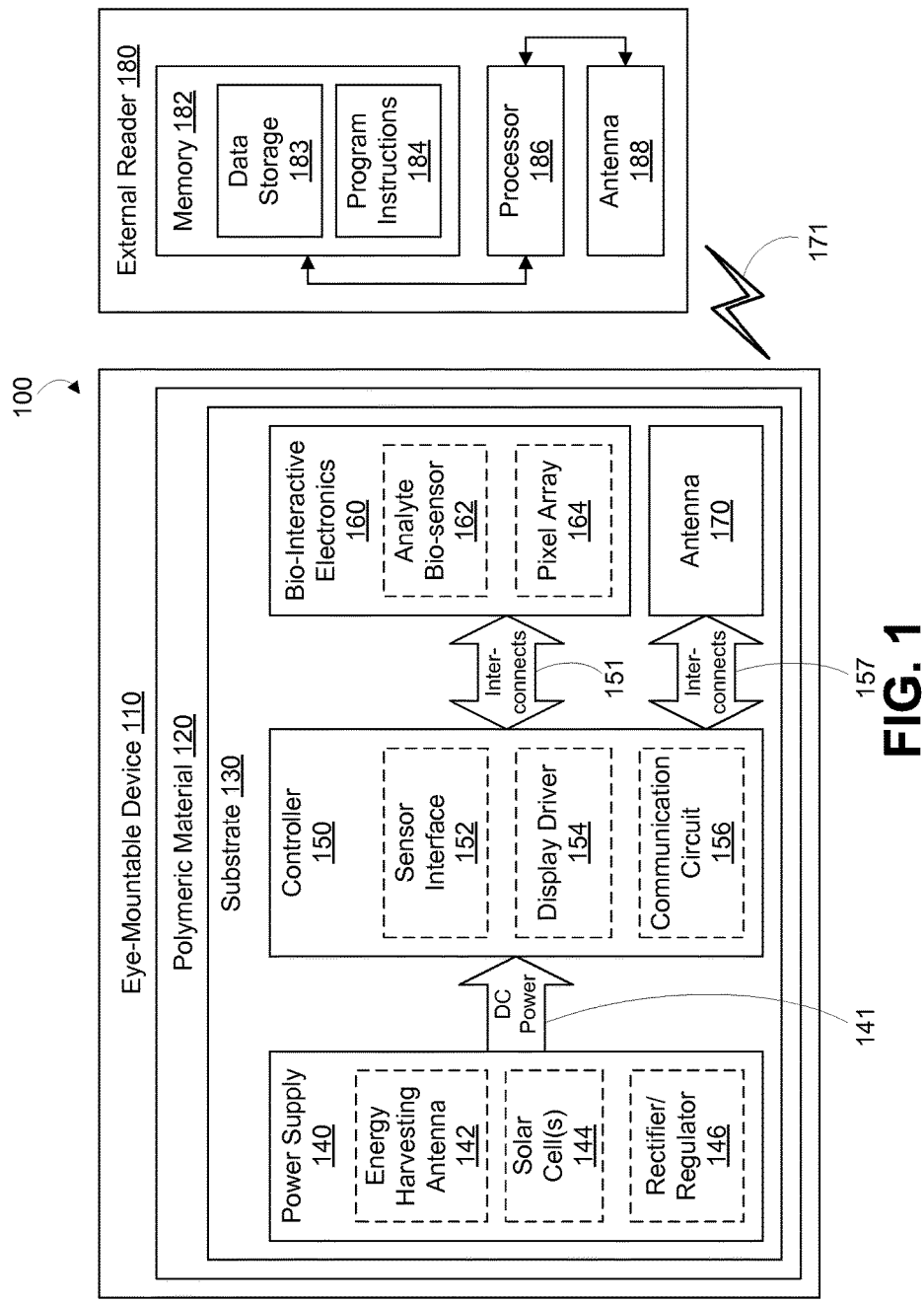
FIG. 1 is a block diagram of a system that includes an eye-mountable device in wireless communication with an external reader, according to an example embodiment.

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. It will be readily understood that certain aspects of the disclosed systems and methods can be arranged and combined in a wide variety of different configurations, all of which are contemplated herein.

I. Introduction

A body-mountable device may include a transparent polymer and an electronic structure embedded in the transparent polymer that has an outer diameter and an inner diameter. The transparent polymer defines a posterior side and an anterior side of the body-mountable device. The electronic structure includes a sensor configured to detect an analyte, and an antenna that includes a plurality of conductive loops spaced apart from each other between the outer diameter and the inner diameter.

As used throughout this disclosure, the anterior side of the body-mountable device refers to an outward-facing side of the body-mountable device, whereas the posterior side of the body-mountable device refers to an inward-facing side of the body-mountable device. In particular, when the body-mountable device comprises an eye-mountable device and the eye-mountable device is mounted on an eye of the user, the anterior side corresponds to a side of the eye-mountable device that is facing outward and thus not touching the eye of the user. Further, when the eye-mountable device is mounted on an eye of the user, the posterior side corresponds to a side of the eye-mountable device that is facing inward and thus touching the eye of the user.

In some embodiments, the transparent polymer may be formed from a posterior polymer layer and an anterior polymer layer, each of which may have a curvature. For instance, when the body-mountable device is an eye-mountable device, characteristics of the posterior polymer layer and the anterior polymer layer may be based on a contact lens prescription of a user of the body-mountable device. The curvature of the posterior polymer layer may correspond to a curvature of the user's cornea, or base curve radius, while the anterior polymer layer may have a curvature sufficient to provide an optical correction to improve the user's vision.

When fabricating the body-mountable device, the electronic structure may be adhered to one of the polymer layers. However, in embodiments where the electronic structure is fabricated on a substantially flat substrate (i.e., a horizontal surface), the electronic structure may have a "memory" that causes the structure to flatten over time. This may result in deformation of the one or both of the polymer layers, and may adversely affect the operability of the body-mountable device.

Beneficially, the embodiments disclosed herein may reduce the tendency for the electronic structure to flatten over time. Prior to adhering the electronic structure to one of the posterior polymer layer or the anterior polymer layer, the electronic structure may be molded to have approximately the same curvature as one (or, in some examples, both) of the polymer layers. Molding the electronic structure may reduce the amount of post-fabrication flattening by the electronic structure, which may reduce the risk of deformations of the body-mountable device.

II. Example Systems and Devices

A body-mountable device may be configured to monitor health-related information based on at least one analyte detected in a fluid of a user wearing the body-mountable device. An example body-mountable device that comprises an eye-mountable device that is configured to detect the at least one analyte in a tear film of a user wearing the eye-mountable device will now be described in greater detail.

FIG. 1 is a block diagram of a system 100 with an eye-mountable device 110 in wireless communication with an external reader 180, according to an example embodiment. The exposed regions of the eye-mountable device 110 are made of a polymeric material 120 formed to be contact-mounted to a corneal surface of an eye. In accordance with exemplary methods, the polymeric material 120 may comprise a first polymer layer and a second polymer layer.

Substrate 130 is embedded in the polymeric material 120 to provide a mounting surface for a power supply 140, a controller 150, bio-interactive electronics 160, and an antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it may also be referred to as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the anterior or outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more bio-compatible materials, such as those employed for use in contact lenses or other ophthalmic applications involving direct contact with the corneal surface. The polymeric material 120 can optionally be formed in part from such bio-compatible materials or can include an outer coating with such bio-compatible materials. The polymeric material 120 can include materials configured to moisturize the corneal surface, such as hydrogels and the like. In some instances, the polymeric material 120 can be a deformable ("non-rigid") material to enhance wearer comfort. In some instances, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 130 to form circuitry, electrodes, etc. For example, the antenna 170 can be formed by depositing a pattern of gold or another conductive material on the substrate 130. Similarly, interconnects 151, 157 between the controller 150 and the bio-interactive electronics 160, and between the controller 150 and the antenna 170, respectively, can be formed by depositing suitable patterns of conductive materials on the substrate 130. A combination of resists, masks, and deposition techniques can be employed to pattern materials on the substrate 130.

The substrate 130 can be a relatively rigid polymeric material, such as polyethylene terephthalate ("PET"), parylene, or another material sufficient to structurally support the circuitry and/or electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from a center of the eye-mountable device 110 and thereby avoid interference with light transmission to the eye through the center of the eye-mountable device 110. For example, where the eye-mountable device 110 is shaped as a concave-curved disk, the substrate 130 can be embedded around the periphery (e.g., near the outer circumference) of the disk. In some embodiments, the bio-interactive electronics 160 (and the substrate 130) can be positioned in a center region of the eye-mountable device 110. The bio-interactive electronics 160 and/or the substrate 130 can be substantially transparent to incoming visible light to mitigate interference with light transmission to the eye. Moreover, in some embodiments, the bio-interactive electronics 160 can include a pixel array 164 that emits and/or transmits light to be perceived by the eye according to display driver instructions. Thus, the bio-interactive electronics 160 can optionally be positioned in the center of the eye-mountable device so as to generate perceivable visual cues to a wearer of the eye-mountable device 110, such as by displaying information via the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a 1 centimeter diameter, a radial thickness of approximately 1 millimeter, and a thickness of about 50 micrometers. The substrate 130 can optionally be aligned with the curvature of the anterior side of the eye-mountable device 110.

The power supply 140 is configured to harvest ambient energy to power the controller 150 and the bio-interactive electronics 160. For example, a radio-frequency energy harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system (not shown) can be included to capture energy from ambient vibrations. The energy-harvesting antenna 142 can optionally be a dual-purpose antenna that is also used to communicate information to the external reader 180. That is, the functions of the antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the energy harvesting antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices arranged to mitigate high frequency variations in the ambient energy harvesting antenna 142 and/or solar cell(s) 144. For example, an energy storage device (e.g., capacitor, inductor, etc.) can be connected to the output of the rectifier/regulator 146 so as to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such as an analyte bio-sensor 162, in bio-interactive electronics 160 to obtain input from the biological environment. Alternatively or additionally, the interaction could involve the use of one or more components, such as the pixel array 164, to provide an output to the biological environment.

In one example, a sensor interface module 152 can be included for operating the analyte bio-sensor 162. The analyte bio-sensor 162 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 152 can be a potentiostat configured to apply a voltage difference between the working and reference electrodes while measuring a current through the working electrode.

In some embodiments, at least a portion of the bio-interactive electronics 160, the controller 150, the power supply, and/or the antenna 170 can be embedded in the substrate 130. And, in some embodiments, at least a portion of the bio-interactive electronics 160 (e.g., the analyte bio-sensor 162) can be surrounded by the substrate 130, except for a surface of the at least a portion of the bio-interactive electronics 160 being exposed by an opening in the substrate 130.

In some instances, a reagent can also be included to sensitize the electrochemical sensor to desired analytes. For example, a layer of glucose oxidase ("GOX") can be situated around the working electrode to catalyze glucose into hydrogen peroxide ($H_2O_2$). The hydrogen peroxide can then be oxidized at the working electrode, which releases electrons to the working electrode, which generates a current.

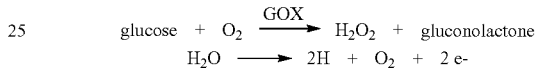

$$\text{glucose} + O_2 \xrightarrow{\text{GOX}} H_2O_2 + \text{gluconolactone}$$
$$H_2O \longrightarrow 2H + O_2 + 2e-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules flow and/or diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the external reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the antenna 170 can be implemented with the same physical antenna. For example, a loop antenna can both harvest incident radiation for power generation and communicate information via backscatter radiation.

The external reader 180 includes an antenna 188 (or group of more than one antenna) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g., RAM) or non-volatile (e.g., ROM) storage system readable by the processor 186. The memory 182 can include a data storage 183 to store indications of data substrates, such as sensor readings (e.g., from the analyte bio-sensor 162), program settings (e.g., to adjust behavior of the eye-mountable device 110 and/or external reader 180), etc. The memory can also include program instructions 184 for execution by the processor 186 to cause the external reader to perform processes specified by the program instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged into a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earring, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the substrate of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the antenna 170) are rectified and/or regulated in the rectifier/regulator 146 and a regulated DC supply voltage 647 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162 sufficient to cause the analyte to undergo an electrochemical reaction at the working electrode. The current through the working electrode can be measured to provide the sensor output indicative of the analyte concentration. The controller 150 can operate the antenna 170 to communicate the sensor results back to the external reader 180 (e.g., via the communication circuit 156). The sensor result can be communicated by, for example, modulating an impedance of the antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the on-board controller 150 and the bio-interactive electronics 160. For example, radio frequency radiation 171 can be supplied to power the eye-mountable device 110 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Figure 2A:
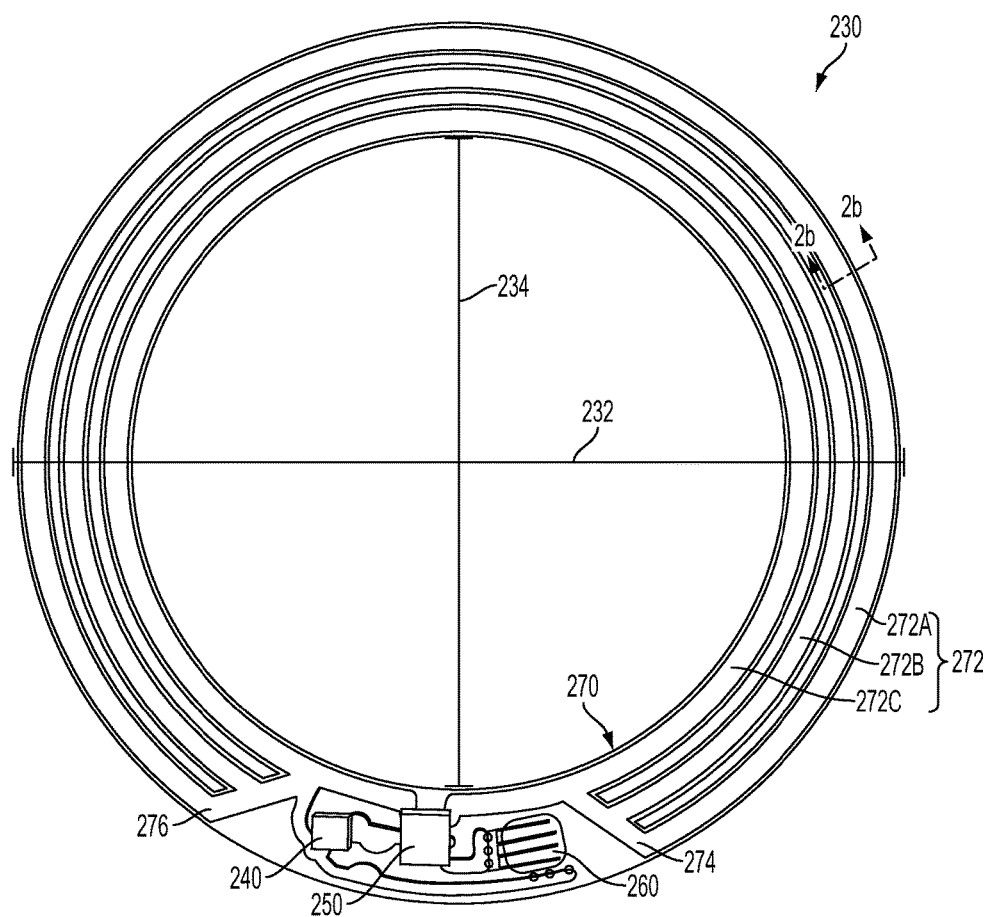
FIG. 2A is a top view of a structure, according to an example embodiment.

FIG. 2A is a top view of an electronic structure 230, according to an example embodiment. In particular, the electronic structure 230 has an outer diameter 232 and an inner diameter 234 and includes electronics 240, electronics 250, a sensor 260, and an antenna 270 disposed thereon. The electronic structure 230 may take the form of or be similar in form to the substrate 130.

The electronic structure 230 can have various sizes. For instance, the size of the electronic structure 230 may depend on which analyte an eye-mountable device is configured to detect. In an example, the electronic structure 230 has a maximum height of approximately 50 between 150 micrometers. Of course, other maximum heights of the electronic structure 230 are possible as well.

In an example, the electronic structure 230 has a height dimension of at least 50 micrometers. In other words, at some point of the electronic structure 230, the height of the electronic structure 230 may be at least 50 micrometers. In an example, this height dimension may correspond to a maximum height of the electronic structure 230. In accordance with the present disclosure, the maximum height of the electronic structure 230 corresponds to the height of the electronic structure 230 at its highest point. For instance, in the example where the electronic structure 230 comprises the sensor 260 and the electronics 250, the height of the electronic structure 230 may vary (and thus the electronic structure 230 may have various height dimensions). For example, the height of the electronic structure 230 may be higher at a point where the electronics 250 is mounted on the electronic structure 230, whereas the height may be lower at a point where there is no chip on the electronic structure 230. In such an example, the maximum height may correspond to the point where the electronics 250 is mounted on the electronic structure 230.

The outer diameter 232 and the inner diameter 234 could take various different forms in various different embodiments. In some embodiments, the outer diameter can have a length between 12.5 and 15 millimeters. Moreover, in some embodiments, the inner diameter can have a length greater than 8 millimeters. And other lengths of the outer diameter 232 and/or inner diameter 234 are possible as well.

The electronics 240 and 250 could be configured in a variety of ways. For example, the electronics 240 and/or the electronics 250 may be configured to operate the sensor 260 and the antenna 270. And, in such an example, the electronics 240 and/or the electronics 250 may be configured for wireless communication with an external reader, such as the external reader 180. In some embodiments, the electronics 240 and the electronics 250 may provide a bias voltage for the sensor 260 and adjust backscattered radio frequency (RF) that is proportional to a current that is passing through the sensor 260.

The electronics 240 and the electronics 250 could take various different forms in various different embodiments. In some embodiments, the electronics 240 and/or the electronics 250 can comprise a chip including one or more logical elements. The electronics 240 and/or the electronics 250 may take the form of or be similar in form to the controller 150.

The sensor 260 is configured to detect one or more analytes. The sensor 260 could take various different forms in various different embodiments. In some embodiments, the sensor 260 can comprise a pair of electrodes, such as a working electrode and a reference electrode. The sensor 260 may take the form of or be similar in form to the analyte bio-sensor 162.

The antenna 270 is configured for communications and/or harvesting energy as described herein. The antenna 270 includes a plurality of conductive loops 272 spaced apart from each other between the outer diameter 232 and the inner diameter 234. In the illustrated example, the plurality of conductive loops 272 includes three conductive loops 272A, 272B, and 272C. However, in other examples, a plurality of conductive loops may include more than three conductive loops, such as five conductive loops, nine conductive loops, etc.

As shown in FIG. 2A, the conductive loops 272A, 272B, and 272C are connected in parallel. With this arrangement, each of the conductive loops in the plurality of conductive loops 272 is electrically connected to the electronics 240, the electronics 250, and the sensor 260 via a first connection 274 and a second connection 276. And the electronics 240, the electronics 250, and the sensor 260 are electrically connected via the first connection 274 and the second connection 276. The first connection 274 and the second connection 276 may take the form of or be similar in form to the interconnects 151 and 157. Moreover, as shown in FIG. 2A, the conductive loops 272A, 272B, and 272C are substantially concentric. The term "substantially concentric," as used in this disclosure, refers to exactly concentric and/or one or more deviations from exactly concentric that do not significantly impact embedding a structure in a body-mountable device as described herein.

And as shown in FIG. 2A, the conductive loops 272A, 272B, and 272C are spaced apart from each other between the outer diameter 232 and the inner diameter 234. In an example, the conductive loops 272A, 272B, and 272C can be spaced apart from adjacent conductive loops by a distance between 100 to 200 micrometers. Other distances are possible as well.

In some embodiments, one of the conductive loops 272A, 272B, and 272C can have a width of 333 micrometers. Other widths of the conductive loops 272A, 272B, and 272C are possible as well. Moreover, in some embodiments, the conductive loops 272A, 272B, and 272C can each have the same width (e.g., the conductive loops 272A, 272B, and 272C can each have a width of 333 micrometers). However, in some embodiments, the conductive loops 272A, 272B, and 272C might not have the same width.

Figure 2B:
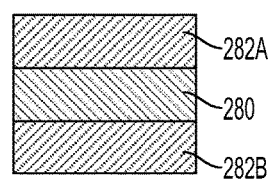
FIG. 2B is a side cross-section view of the structure shown in FIG. 2A, according to an example embodiment.

Each conductive loop in the plurality of conductive loops 272 can comprise a respective metal layer disposed between respective polymer layers. With this arrangement, the polymer layers might block moisture from the metal layer. FIG. 2B is a side cross-section view of the structure shown in FIG. 2A, according to an example embodiment. As shown in FIG. 2B, the conductive loop 272A comprises a metal layer 280 disposed between polymer layers 282A and 282B. The respective metal layers of the conductive loops 272B and 272C may take the form of or be similar in form to the to the metal layer 280, and the respective polymer layers of the conductive loops 272B and 272C may take the form of or be similar in form to the polymer layers 282A and 282B.

In some embodiments, the metal layer 280 can comprise gold or another conductive material that can be deposited on the electronic structure 230, such as platinum, palladium, titanium, carbon, aluminum, copper, silver, and/or silver-chloride. And in at least one such embodiment, the metal layer 280 can have a thickness between 5 and 30 micrometers. Other thicknesses of the metal layer 280 are possible as well. In an example, the metal layer 280 can be formed by a process that includes electroplating.

Moreover, in some embodiments, the polymer layers 282A and 282B can comprise a relatively rigid transparent bio-compatible polymer, such as PET or parylene-C (e.g., dichlorodi-p-xylylene). Each bio-compatible polymer included in the polymer layers 282A and 282B may have an associated glass transition temperature and an associated melting temperature. And in at least such embodiment, the polymer layers 282A and 282B can have a thickness between 10 and 50 micrometers, such as 15 micrometers. Other thicknesses of the polymer layers 282A and 282B are possible as well. In an example, the polymer layers 282A and 282B can be formed by a process that includes chemical vapor deposition.

In an example, the plurality of conductive loops 272 can be formed by a process that includes etching a portion of a metal layer disposed between polymer layers with an inductively coupled plasma, such as an oxygen plasma.

Figure 3A:
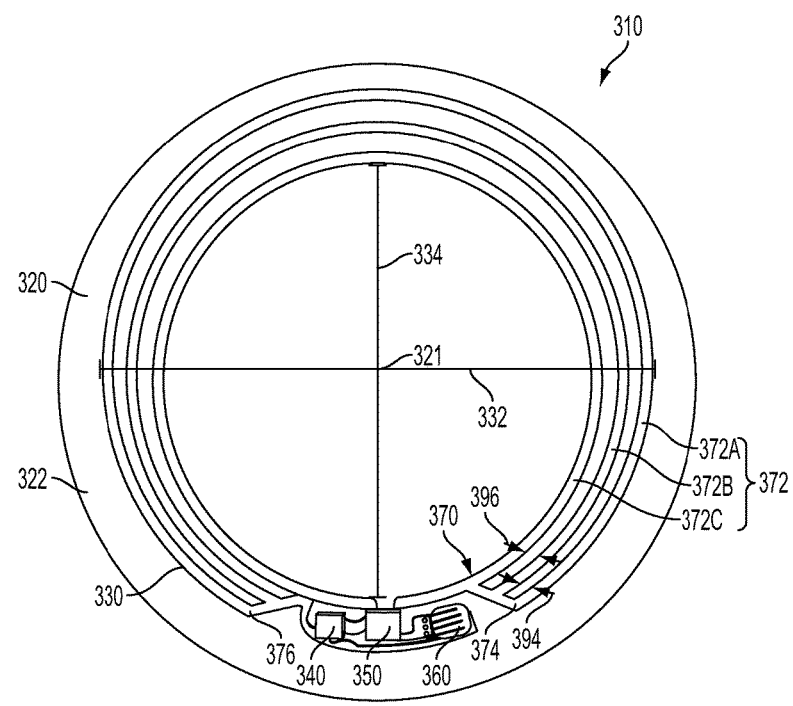
FIG. 3A is a top view of an eye-mountable device, according to an example embodiment.
Figure 3B:
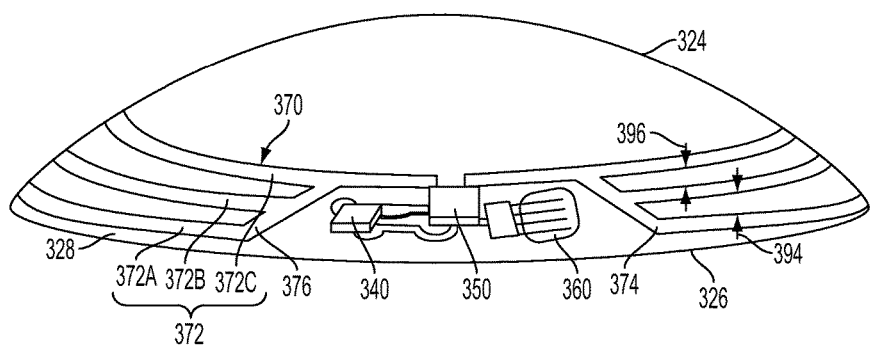
FIG. 3B is a side view of the eye-mountable device shown in FIG. 3A, according to an example embodiment.

FIG. 3A is a top view of an eye-mountable electronic device 310. FIG. 3b is a side view of the eye-mountable electronic device 310 shown in FIG. 3A. It is noted that relative dimensions in FIGS. 3a and 3b are not necessarily to scale, but have been rendered for purposes of explanation only in describing the arrangement of the eye-mountable electronic device 310. The eye-mountable device 310 is formed of a transparent polymer 320 shaped as a curved disk. The transparent polymer 320 can be a substantially transparent material to allow incident light to be transmitted to the eye while the eye-mountable device 310 is mounted to the eye. The transparent polymer 320 can be a bio-compatible material similar to those employed to form vision correction and/or cosmetic contact lenses in optometry, such as PET, polymethyl methacrylate ("PMMA"), silicone hydrogels, combinations of these, etc. The transparent polymer 320 could take the form of or be similar in form to the polymeric material 120.

The transparent polymer 320 can be formed with one side having a posterior side 326 (i.e., concave surface) suitable to fit over a corneal surface of an eye. The opposing side of the disk can have anterior side 324 (i.e., convex surface) that does not interfere with eyelid motion while the eye-mountable device 310 is mounted to the eye. A circular outer side edge 328 connects the posterior side 326 and anterior side 324.

The eye-mountable device 310 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 310 can be selected according to the size and/or shape of the corneal surface and/or the scleral surface of the wearer's eye.

While the eye-mountable device 310 is mounted in an eye, the anterior side 324 faces outward to the ambient environment while the posterior side 326 faces inward, toward the corneal surface. The anterior side 324 can therefore be considered an outer, top surface of the eye-mountable device 310 whereas the posterior side 326 can be considered an inner, bottom surface. The "top" view shown in FIG. 3A is facing the anterior side 324.

The electronic structure 330 is embedded in the transparent polymer 320. The substrate 330 can be embedded to be situated along an outer periphery 322 of the transparent polymer 320, away from a center region 321. The electronic structure 330 does not interfere with vision because it is too close to the eye to be in focus and is positioned away from the center region 321 where incident light is transmitted to the light-sensing portions of the eye. The electronic structure 330 can take the form or be similar in form to the substrate 130 and/or the electronic structure 230.

The electronic structure 330 has an outer diameter 332 and an inner diameter 334 and includes electronics 340, electronics 350, a sensor 360, and an antenna 370 disposed thereon. The outer diameter 332 may take the form of or be similar in form to the outer diameter 232, the inner diameter 334 may take the form of or be similar in form to the inner diameter 234, the electronics 340 may take the form of or be similar in form to the controller 150 and/or the electronics 240, the electronics 350 may take the form or be similar in form to the controller 150 and/or the electronics 250, and the sensor 360 may take the form or be similar in form to the bio-analyte sensor 162 and/or the sensor 260.

The antenna 370 is configured for communications and/or harvesting energy, like the antenna 270 is configured for communications and/or harvesting energy. The antenna 370 includes a plurality of conductive loops 372 spaced apart from each other between the outer diameter 332 and the inner diameter 334. In the illustrated example, the plurality of conductive loops 372 includes three conductive loops 372A, 372B, and 372C. However, in other examples, a plurality of conductive loops may include more than three conductive loops, such as five conductive loops, nine conductive loops, etc. When the electronic structure 330 is embedded in the transparent polymer 320, the conductive loops 372A, 372B, and 372C may move relative to each other.

The conductive loops 372A, 372B, and 372C can have an arrangement similar to an arrangement of the conductive loops 272A, 272B, and 272C. As shown in FIGS. 3a and 3b, the conductive loops 372A, 372B, and 272C are connected in parallel. With this arrangement, each of the conductive loops in the plurality of conductive loops 372 is electrically connected to the electronics 340, the electronics 350, and the sensor 360 via a first connection 374 and a second connection 376. And the electronics 340, the electronics 350, and the sensor 360 are electrically connected via the first connection 374 and the second connection 376. The first connection 374 and the second connection 376 may take the form of or be similar in form to the first connection 274 and the second connection 276 and/or the interconnects 151 and 157. Moreover, as shown in FIGS. 3a and 3b, the conductive loops 372A, 372B, and 372C are substantially concentric. And as shown in FIGS. 3a and 3b, the conductive loops 372A, 372B, and 372C are spaced apart from each other between the outer diameter 332 and the inner diameter 334.

The conductive loops 372A, 372B, and 372C may have a width that is the same or similar to a width of the conductive loops 272A, 272B, and 272C. Moreover, each of the conductive loops in the plurality of conductive loops 372 can comprise a respective metal layer disposed between respective polymer layers, like the conductive loops in the plurality of conductive loops 272 comprise a respective metal layer disposed between respective polymer layers. And the plurality of conductive loops 372 can be formed like the plurality of conductive loops 272 is formed.

In the illustrated example, the metal and polymer layers in each conductive loop in the plurality of conductive loops 372 are spaced apart from the metal and polymer layers in each adjacent conductive loop in the in the plurality of conductive loops 372. In some embodiments, the transparent polymer 320 can extend between adjacent conductive loops (e.g., the conductive loop 372A and the conductive loop 372B and/or the conductive loop 372B and the conductive loop 372C) in the plurality of conductive loops 372.

Moreover, in the illustrated example, the metal and polymer layers of conductive loop 372B are spaced apart from the metal and polymer layers of adjacent conductive loop 372A by a first distance 394, and the metal and polymer layers of conductive loop 372B are spaced apart from the metal and polymer layers of adjacent conductive loop 372C by a second distance 396. In an example, the first distance 394 and the second distance 396 can be between 100 to 200 micrometers. Other distances are possible as well.

The first distance 394 could be a different value than the second distance 396. In some embodiments, the first distance 394 can be greater (or less) than the second distance 396. And the first distance 394 and/or the second distance 396 could vary. In some embodiments, the first distance 394 can vary based on a rotational orientation of the conductive loop 372B relative to the conductive loop 372A and/or the conductive loop 372C. Moreover, in some embodiments, the second distance 396 can vary based on a rotational orientation of the conductive loop 372B relative to the conductive loop 372C and/or the conductive loop 372A.

Figure 3D:
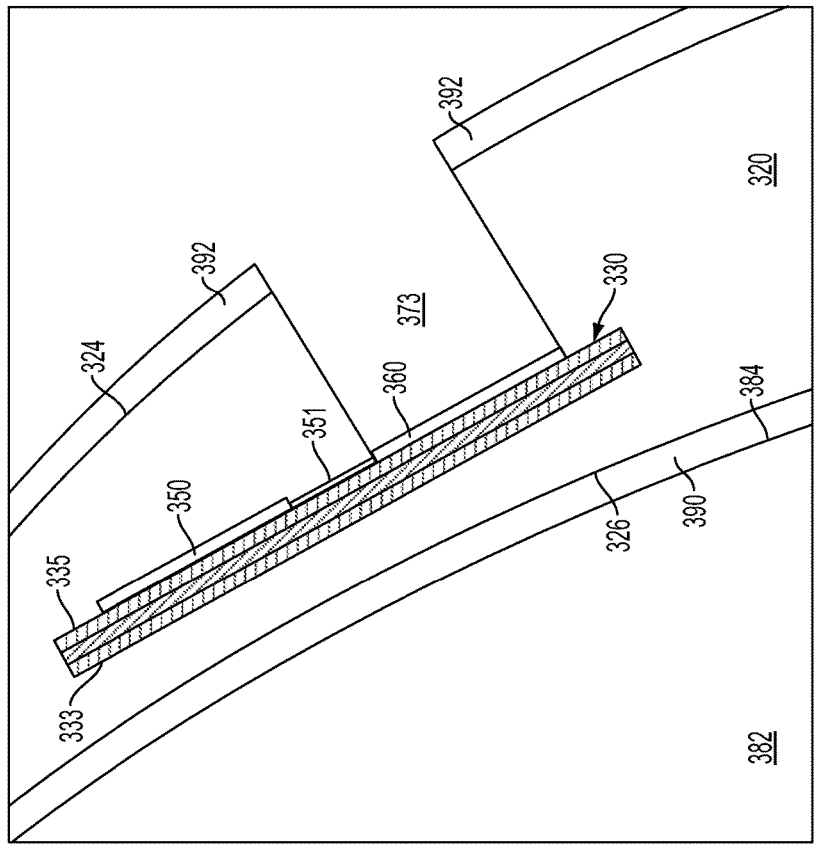
FIG. 3D is a side cross-section view showing tear film layers surrounding the surfaces of the eye-mountable device mounted as shown in FIG. 3C, according to an example embodiment.
Figure 3C:
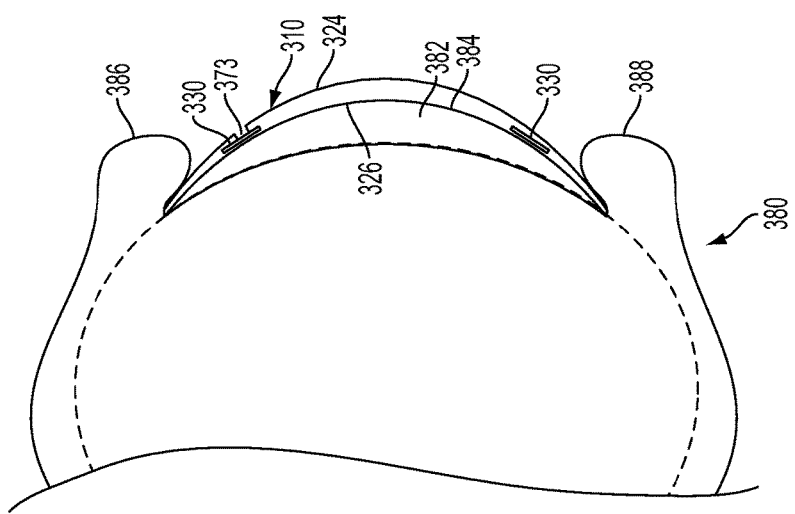
FIG. 3C is a side cross-section view of the eye-mountable device shown in FIG. 3A while mounted to a corneal surface of an eye, according to an example embodiment.

FIG. 3C is a side cross-section view of the eye-mountable 310 while mounted to a corneal surface 384 of an eye 380, according to an example embodiment. FIG. 3D is a close-in side cross-section view enhanced to show tear film layers 390, 392 surrounding exposed surfaces 324, 326 of the eye-mountable device 310, according to an example embodiment. It is noted that relative dimensions in FIGS. 3c and 3d are not necessarily to scale, but have been rendered for purposes of explanation only in describing the arrangement of the eye-mountable electronic device 310. For example, the total thickness of the eye-mountable device 310 can be about 200 micrometers, while the thickness of the tear film layers 390, 392 can each be about 10 micrometers, although this ratio may not be reflected in the drawings. Some aspects are exaggerated to allow for illustration and facilitate explanation.

The eye 380 includes a cornea 382 that is covered by bringing the upper eyelid 386 and lower eyelid 388 together over the top of the eye 380. Incident light is received by the eye 380 through the cornea 382, where light is optically directed to light-sensing elements of the eye 380 (e.g., rods and cones, etc.) to stimulate visual perception. The motion of the eyelids 386, 388 distributes a tear film across the exposed corneal surface 384 of the eye 380. The tear film is an aqueous solution secreted by the lacrimal gland to protect and lubricate the eye 380. When the eye-mountable device 310 is mounted in the eye 380, the tear film coats both the anterior and posterior sides 324, 326 with an inner layer 390 (along the posterior side 326) and an outer layer 392 (along the anterior side 324). The tear film layers 390, 392 can be about 10 micrometers in thickness and together account for about 10 microliters.

The tear film layers 390, 392 are distributed across the corneal surface 384 and/or the posterior side 324 by motion of the eyelids 386, 388. For example, the eyelids 386, 388 raise and lower, respectively, to spread a small volume of tear film across the corneal surface 384 and/or the anterior side 324 of the eye-mountable device 310. The tear film layer 390 on the corneal surface 384 also facilitates mounting the eye-mountable device 310 by capillary forces between the anterior side 326 and the corneal surface 384. In some embodiments, the eye-mountable device 310 can also be held over the eye in part by vacuum forces against the corneal surface 384 due to the concave curvature of the eye-facing anterior side 326.

In some embodiments, a polymer layer defining the anterior side 326 may be greater than 50 micrometers thick, whereas a polymer layer defining the posterior side 324 may be less than 150 micrometers. Thus, when the sensor 360 is mounted on an outward-facing surface 335 (as shown in FIG. 3D) the sensor 360 may be at least 50 micrometers away from the anterior side 324 and may be a greater distance away from the posterior side 326. However, in other examples, the sensor 360 may be mounted on an inward-facing surface 333 of the electronic structure 330 such that the sensor 360 is facing the posterior side 326. The sensor 360 could also be positioned closer to the anterior side 324 than the posterior side 326. With this arrangement, the sensor 360 can receive analyte concentrations in the tear film 392 via a channel 373. In some examples, analyte concentrations in the tear film 390 and/or 392 may diffuse through the transparent polymer 320 to the sensor 360. As a result, the eye-mountable device 310 might not include the channel 373.

While the body-mountable device has been described as comprising the eye-mountable device 110 and/or the eye-mountable device 310, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 310. For instance, the tooth-mountable device could include a polymeric material or a transparent polymer that is the same or similar to any of the polymeric materials or transparent polymers described herein and a substrate or a structure that is the same or similar to any of the substrates or structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 310. For instance, the skin-mountable device could include a polymeric material or a transparent polymer that is the same or similar to any of the polymeric materials or transparent polymers described herein and a substrate or a structure that is the same or similar to any of the substrates or structures described herein. With such an arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 4:
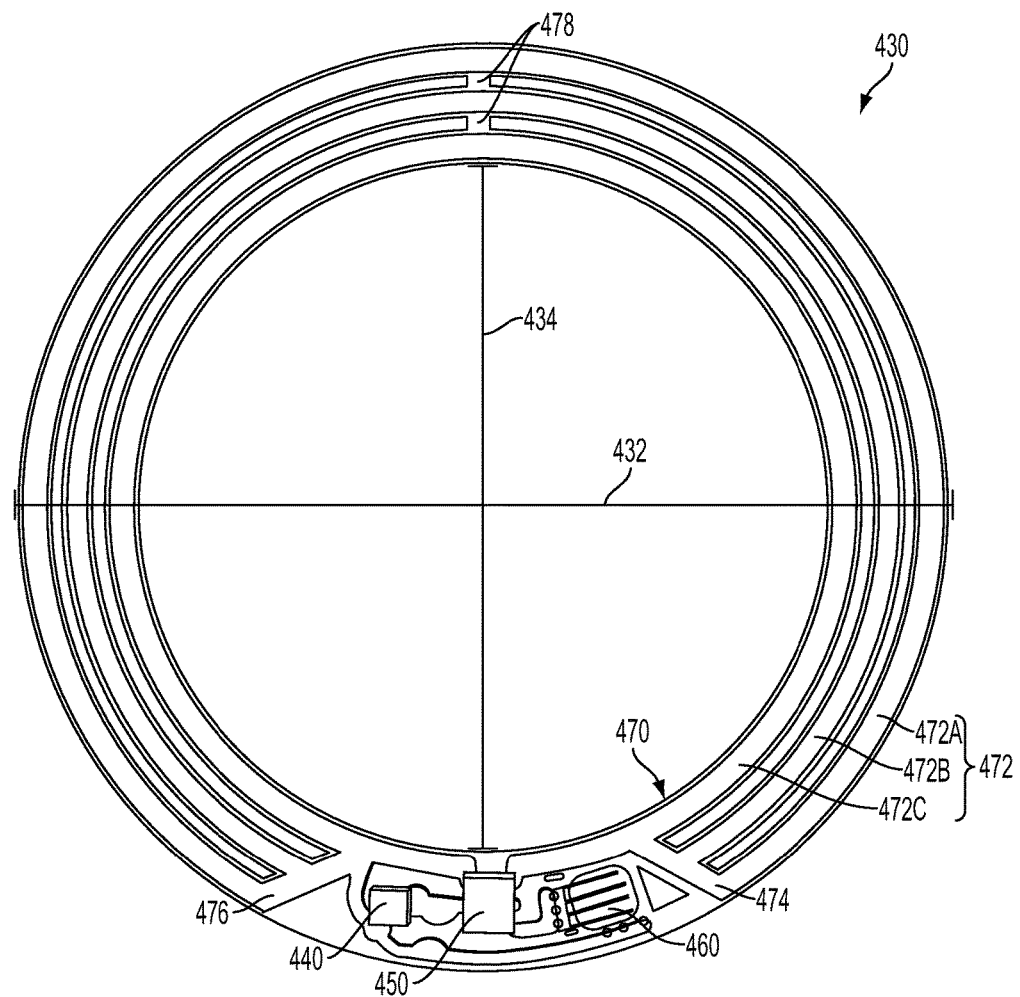
FIG. 4 is a top view of another structure, according to an example embodiment.

FIG. 4 is a top view of a structure 430, according to an example embodiment. In particular, the electronic structure 430 includes a spacer 478 configured to maintain substantially uniform spacings between adjacent conductive loops in a plurality of conductive loops 472. The term "substantially uniform," as used in this disclosure, refers to exactly uniform and/or one or more deviations from exactly uniform that do not significantly impact embedding an structure in a body-mountable device as described herein.

More specifically, the electronic structure 430 has an outer diameter 432 and an inner diameter 434 and includes electronics 440, electronics 450, a sensor 460, and an antenna 470 disposed thereon. The outer diameter 432 may take the form of or be similar in form to the outer diameter 232 and/or the outer diameter 332; the inner diameter 434 may take the form of or be similar in form to the inner diameter 234 and/or the inner diameter 334; the electronics 440 may take the form of or be similar in form to the controller 150, the electronics 240, and/or the electronics 340, the electronics 450 may take the form or be similar in form to the controller 150, the electronics 250, and/or the electronics 350; and the sensor 460 may take the form or be similar in form to the bio-analyte sensor 162, the sensor 260, and/or the sensor 360.

The antenna 470 is configured for communications and/or harvesting energy, like the antenna 270 and the antenna 370 are configured for communications and/or harvesting energy. As noted, the antenna 470 includes the plurality of conductive loops 472. The plurality of conductive loops 472 is spaced apart from each other between the outer diameter 432 and the inner diameter 434. In the illustrated example, the plurality of conductive loops 472 includes three conductive loops 472A, 472B, and 472C. However, in other examples, a plurality of conductive loops may include more than three conductive loops, such as five conductive loops, nine conductive loops, etc.

The conductive loops 472A, 472B, and 472C can have an arrangement similar to an arrangement of the conductive loops 272A, 272B, and 272C and/or the conductive loops 372A, 372B, and 372C. As shown in FIG. 4, the conductive loops 472A, 472B, and 472C are connected in parallel. With this arrangement, each of the conductive loops in the plurality of conductive loops 472 is electrically connected to the electronics 440, the electronics 450, and the sensor 460 via a first connection 474 and a second connection 476. And the electronics 440, the electronics 450, and the sensor 460 are electrically connected via the first connection 474 and the second connection 476. The first connection 474 and the second connection 476 may take the form of or be similar in form to the interconnects 151 and 157, the first connection 274 and the second connection 276, and/or the first connection 374 and the second connection 376.

Moreover, as shown in FIG. 4, the conductive loops 472A, 472B, and 472C are substantially concentric. And as shown in FIG. 4, the conductive loops 472A, 472B, and 472C are spaced apart from each other between the outer diameter 432 and the inner diameter 434. In an example, the conductive loops 472A, 472B, and 472C can be spaced apart from adjacent conductive loops by a distance between 100 to 200 micrometers. Other distances are possible as well.

The conductive loops 472A, 472B, and 472C may have a width that is the same or similar to a width of the conductive loops 272A, 272B, and 272C and/or the conductive loops 372A, 372B, and 372C. Moreover, each of the conductive loops in the plurality of conductive loops 472 can comprise a respective metal layer disposed between respective polymer layers, like the conductive loops in the plurality of conductive loops 272 comprise a respective metal layer disposed between respective polymer layers. And the plurality of conductive loops 472 can be formed like the plurality of conductive loops 272 and/or the plurality of conductive loops 372 is formed.

The electronic structure 430 may be embedded in a transparent polymer, such as the transparent polymer 320. For instance, when the electronic structure 430 is embedded in the transparent polymer, when each of the conductive loops in the plurality of conductive loops 472 comprise a respective metal layer disposed between respective polymer layers, the metal and polymer layers in each conductive loop in the plurality of conductive loops 472 can be spaced apart from the metal and polymer layers in each adjacent conductive loop in the plurality of conductive loops 472. And the transparent polymer can extend between adjacent conductive loops in the plurality of conductive loops 472.

As noted, the electronic structure 430 includes the spacer 478. When the electronic structure 430 is embedded in the transparent polymer the conductive loops 472A, 472B, and 472C may not move relative to each other based on the spacer 478.

As shown in FIG. 4, the spacer 478 is connected to the conductive loops 472A, 472B, and 472C and is located on the electronic structure 430 substantially opposite of the sensor 260. Other locations of the spacer 478 on the electronic structure 430 are possible as well. For instance, the spacer 478 could be located on the electronic structure 430 at a predetermined rotational orientation, such as 30°, 45°, 60°, 90°, etc. The term "substantially opposite," as used in this disclosure, refers to exactly opposite (e.g., a rotational orientation of 180°) or one or more deviations from exactly opposite that do not significantly impact embedding a structure in a body-mountable device as described herein.

The spacer 478 could take various different forms in various different embodiments. For example, in some embodiments, the spacer 478 can have a width between 50 and 300 micrometers. Other widths of the spacer 478 are possible as well. Moreover, in some embodiments, the spacer 478 can comprise a metal, such as gold, platinum, palladium, titanium, aluminum, copper, and/or silver. In some examples, the spacer 478 can comprise the same metal as the respective metal layers of the conductive loops 472A, 472B, and 472C. However, in other examples, the spacer 478 can comprise a different metal than the respective metal layers of the conductive loops 472A, 472B, and 472C. In an example, the spacer 478 can be formed by a process that includes electroplating.

Furthermore, in some embodiments, the spacer 478 can comprise a polymeric material, such as PET or paralyene. In some examples, the spacer 478 can comprise the same polymeric material as the respective polymer layers of the conductive loops 472A, 472B, and 472C. However, in other examples, the spacer 478 can comprise a different polymeric material than the respective polymer layers of the conductive loops 472A, 472B, and 472C. In an example, the spacer 478 can be formed by a process that includes chemical vapor deposition.

And in some embodiments, the spacer 478 can comprise a metal layer disposed between polymer layers, like the respective metal layers disposed between the respective polymer layers of the conductive loops 472A, 472B, and 472C.

In an example, the spacer 478 is formed by a process that includes etching a portion of a metal and/or a polymeric material with an inductively coupled plasma, such as an oxygen plasma.

In the illustrated example, the electronic structure 430 includes one spacer, the spacer 478. However, in other examples, a structure may include more than one spacer, such as two spacers, three spacers, four spacers, etc. For instance, a structure could include one or more spacers configured to maintain substantially uniform spacings between adjacent conductive loops in a plurality of conductive loops. And each spacer in the one or more spacers could be located on the structure in a predetermined rotational orientation, such as 30°, 45°, 60°, 90°, etc. Each of the spacers in the one or more spacers could take the form or be similar in form to the spacer 478.

III. Example Methods

Each of the electronic structures 230, 330, 430 may be fabricated on a substantially flat surface. Moreover, each of the described electronic structures may have a "memory" characteristic. That is, if the electronic structure is adhered to a polymer layer such that the electronic device has a curvature, the memory characteristic of the electronic device may cause the electronic structure to flatten over time.

Figure 5A:
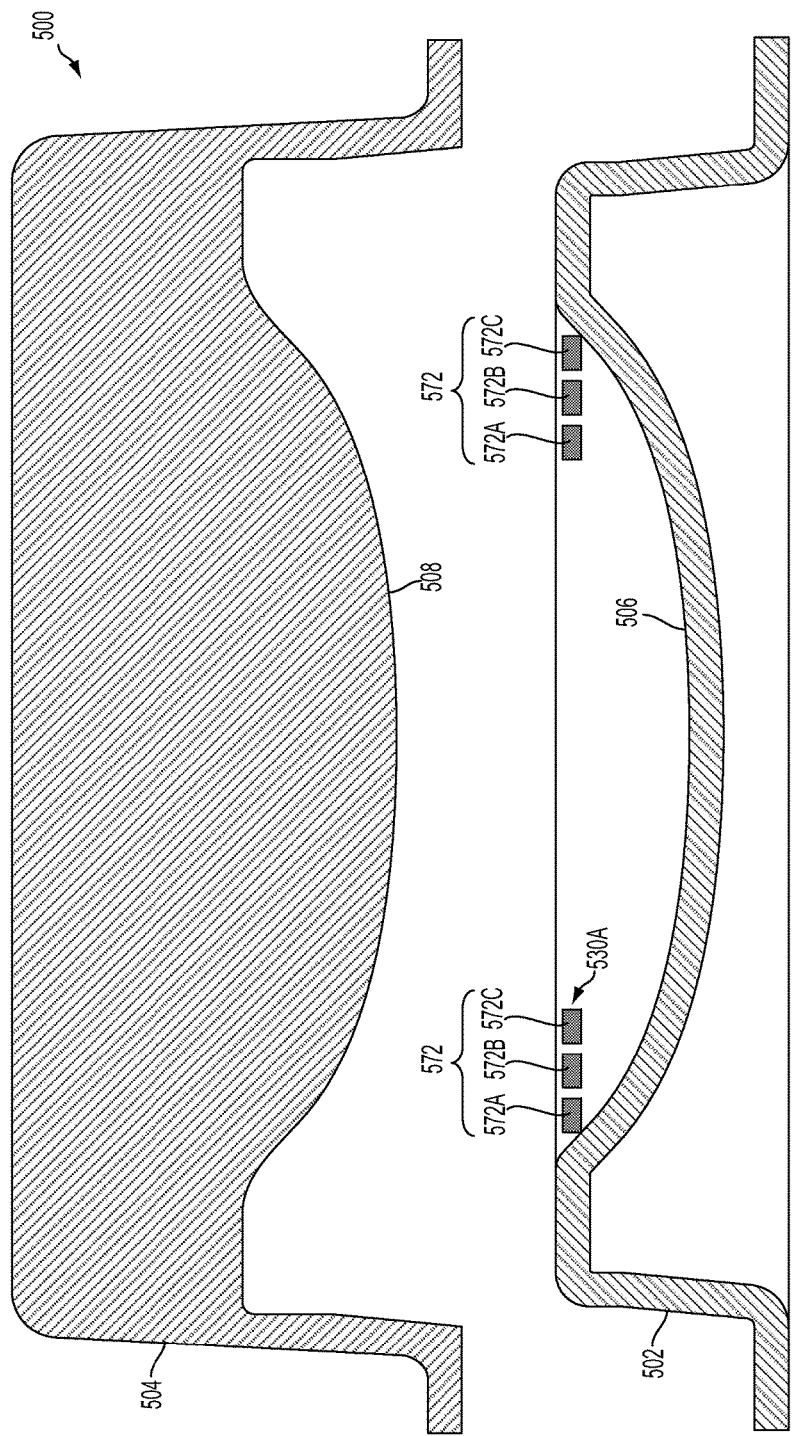
FIG. 5A-C show stages for molding an electronic structure, according to an example embodiment.
Figure 5B:
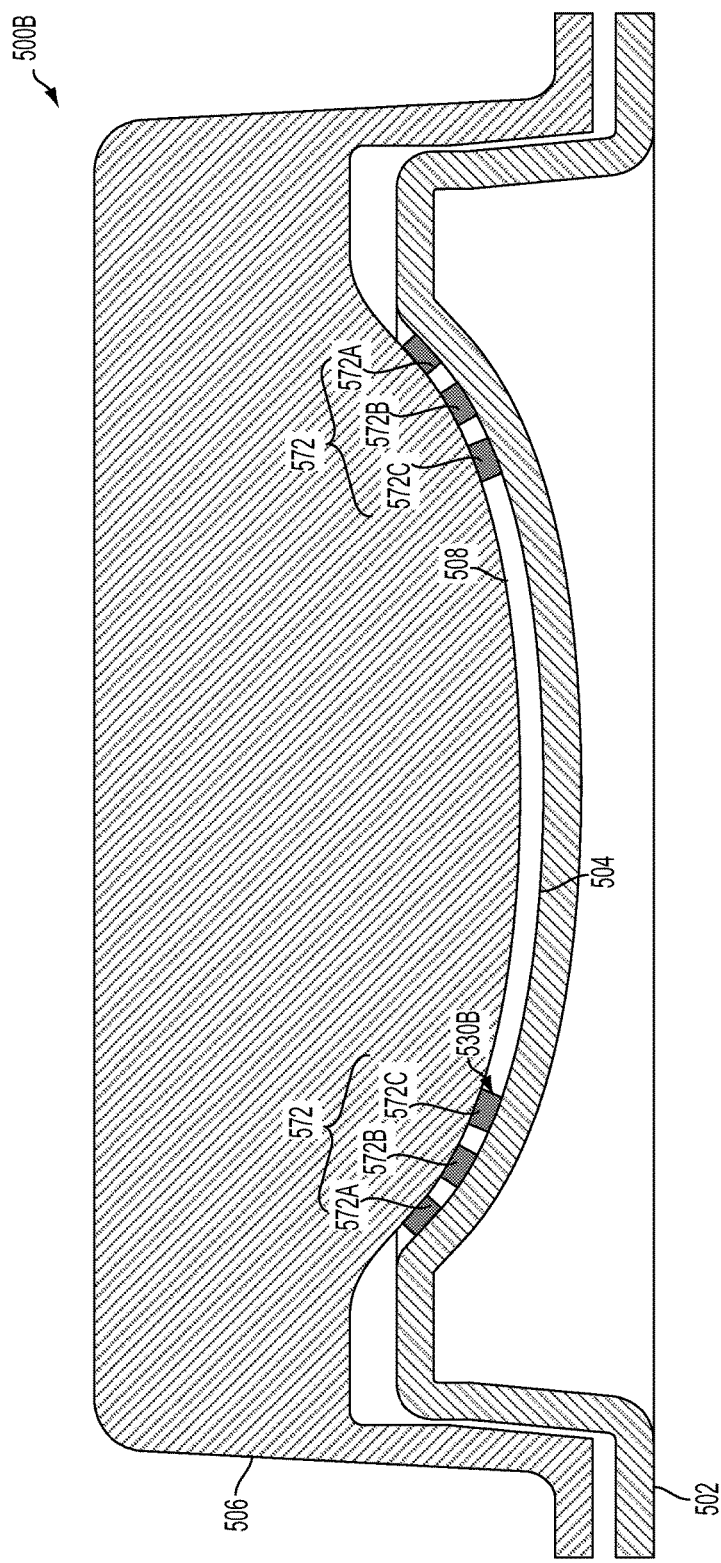
Figure 5C:
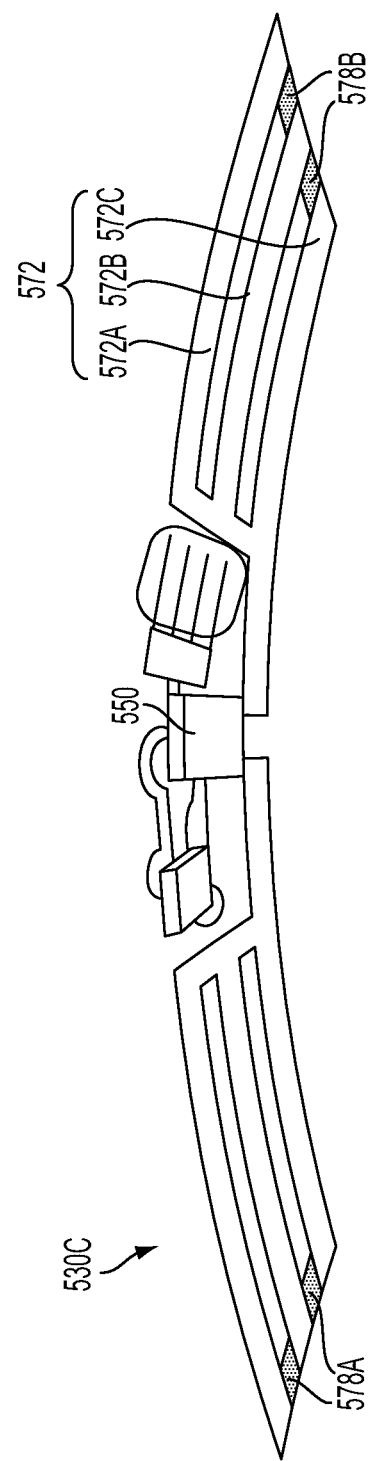

To minimize the amount of flattening of the electronic structures 230, 330, 430, the electronic structures 230, 330, 430 may be molded to have a first curvature. FIGS. 5A-C illustrate stages in a process for molding an electronic structure configured for use in body-mountable device, such as a molded electronic structure 530 shown in FIG. 5C.

FIG. 5A shows a cross-sectional view of a molding apparatus 500 that includes a lower molding piece 502 and an upper molding piece 504. As shown in FIG. 5A, an electronic structure 530A is inserted into a mold cavity 506 of the lower molding piece 502. The electronic structure 530A may be the same as or substantially similar to any one of the electronic structures 230, 330, 430 described with respect to FIGS. 2-4, respectively. Similarly, a plurality of conductive loops 570 may be the same as or substantially similar to any one of the plurality of conductive loops 270, 370, 470, and conductive loops 572A-C may be the same as or substantially similar to the conductive loops 272A-C, 372A-C, 472A-C. Additionally, the conductive loops 572A-C may be substantially concentric rings, as illustrated in FIG. 5A.

The upper mold 504 may be substantially centered over the lower mold 502. Additionally, the lower mold 502 and/or the upper mold 504 may include cutouts (not shown) for components of the compressed electronic structure 530A, such as electronics components and/or sensor components (e.g., the electronics 250, 350, 450 and the sensors 260, 360, 460 described with respect to FIGS. 2-4, respectively).

The mold cavity 506 may be concave and have a radius of curvature. The radius of curvature of the mold cavity 506 may depend on a number of factors. In one example, the radius of curvature of the mold cavity 506 may be the same as or substantially similar to the radius of curvature of a polymer layer of a body-mountable device. In an eye-mountable device, for instance, the radius of curvature of the mold cavity 506 may correspond to a radius of curvature of one of a user's cornea (i.e., a base curve radius for the user's cornea). In another example, however, the radius of curvature of the mold cavity 506 may be the same as or substantially similar to the anterior polymer layer of a body-mountable device. In yet another example, the radius of curvature of the mold cavity 506 may be selected to be between the radii of curvature of the posterior polymer layer and the anterior polymer layer.

Moreover, the radius of curvature of the mold cavity 506 may be less than the radius of curvature of the posterior polymer layer. In some embodiments, the radius of curvature of a molded electrical structure may flatten slightly over time, which may correspond to an increase in the radius of curvature of the molded electrical structure. The increase in the radius of curvature may be estimated, perhaps by measuring the increase in the radius of curvature of other molded electronic structures over a period of time. The radius of curvature of the mold cavity 506 may account for the estimated increase in the radius of curvature of the molded electrical structure.

As one example, the radius of curvature of the mold cavity 506 may be the radius of curvature of one of the polymer layers of the body-mountable device minus an offset. The offset may be based on the estimated increase in the radius of curvature of a molded electronic structure. Further, the offset may be within a tolerance of ranges. For instance, if the anticipated increase in a molded electrical structure is approximately 0.5 mm, the offset may be 0.5 mm+/−0.2 mm. Other offsets and/or tolerances may also be used in other examples.

The upper mold 504 includes a convex molding surface 508. The radius of curvature of the molding surface 508 may be the same as or substantially similar to the radius of curvature of the mold cavity 506. When the molding surface 508 is inserted into the mold cavity 506, the conductive loops 572A-C may be compressed between the mold cavity 504 and the upper surface 508, which may cause the molded electronic structure 530A to have a radius of curvature that is approximately equal to the radius of curvature of the mold cavity 504.

FIG. 5B shows a compressed electronic structure 530B that is compressed by the molding apparatus 500 in the mold cavity 506 by the molding surface 508. The compressed electronic structure 530B comprises the same components as the electronic structure 530A depicted in FIG. 5A.

A force used to compress the compressed electronic structure 530B may generally depend on the materials and components of the compressed electronic structure 530B. That is, the compression force may be sufficient to cause the plurality of conductive loops 572 to conform to the shape of the mold cavity 504 without damaging the components of the compressed electronic structure 530B.

During the molding process, the compressed electronic device 530B may be baked by heating the molding apparatus 500 to a predetermined temperature and maintaining the predetermined temperature for a period of time. The predetermined temperature and the period of time may depend on one or more of the materials used to form the electronic structure. In one example, the compressed electronic device 530B may comprise a layer of a bio-compatible polymer. The predetermined temperature may be greater than a glass transition temperature and less than a melting temperature of the bio-compatible polymer. The period of time may depend on the predetermined temperature. That is, the period of time may be longer for lower predetermined temperatures than for higher predetermined temperatures. For instance, the compressed electronic structure 530B may include a layer of parylene-C. In this example, the predetermined temperature may be between 90° C. and 150° C., and, more specifically, between 90° C. and 110° C. The period of time may vary from a few minutes to ninety minutes or more, depending on the predetermined temperature.

After baking is complete, the compressed structure 530B may be cooled and removed from the molding apparatus 500 to provide a molded electronic structure. FIG. 5C shows a side profile of a molded electronic structure 530C. The molded electronic structure 530C may have a radius of curvature that is the same as or substantially similar to the radius of curvature of the mold cavity 504 of the lower mold 502.

FIG. 5C also shows spacers 578A and 578B. The spacers 578A, 578B are the same as or are substantially similar to the spacer 478 described with respect to FIG. 4. In addition to separating the conductive loops 572A-C, the spacers 578A, 578B may also provide additional support for the molded electronic structure 530.

The spacers 578A, 578B may be composed of a material that does not have a "memory." That is, the spacers 578A, 578B may not have a tendency to return to their initial, pre-mold shape. In this regard, the spacers 578A, 578B may reduce or otherwise limit the change in the radius of curvature (i.e., flattening of the curvature over time) of the molded electronic structure 530C. Consequently, the spacers 578A, 578B may further reduce the likelihood of deformations in a body-mountable device that includes the molded electronic structure 530C.

In the molded electronic structure 530C, the spacers 578A, 578B are substantially opposite from one another. That is, the spacers 578A, 578B are approximately 180° apart from one another. In other embodiments, however, the molded electronic structure 530C may include more or fewer spacers. For instance, the molded electronic structure 530C may include one spacer that is substantially opposite from the electronics 550. Other configurations of spacers may also be possible.

Figure 6:
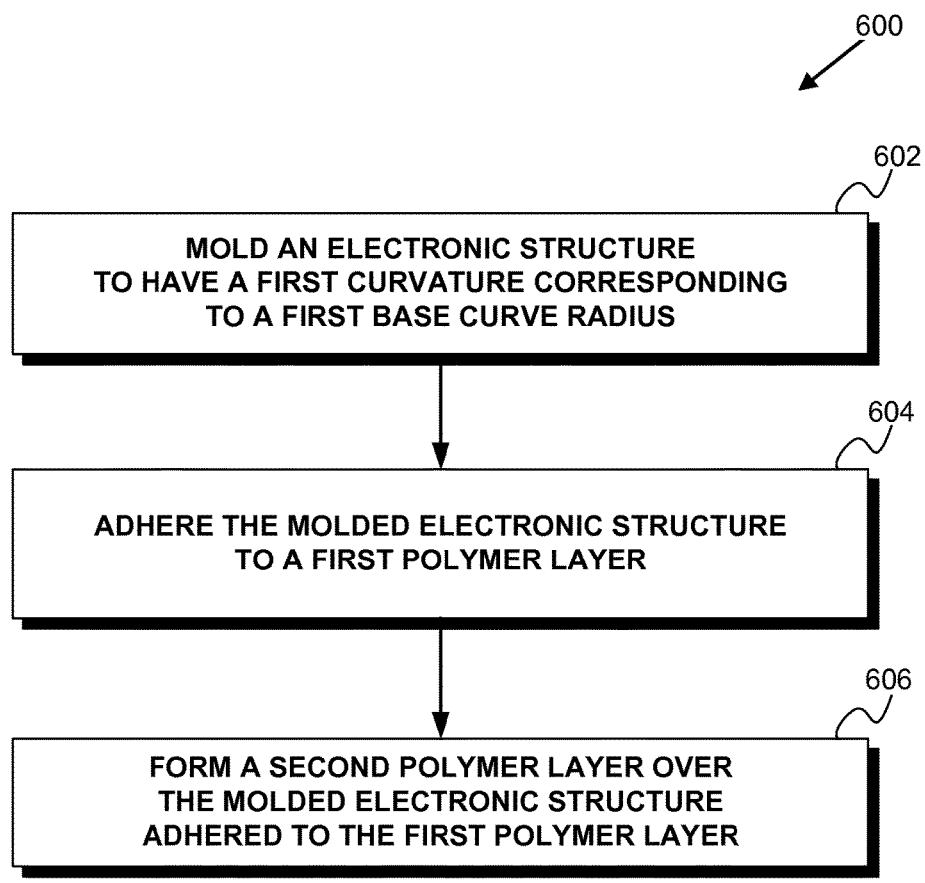
FIG. 6 is a flow chart illustrating a method, according to an example embodiment.

FIG. 6 is a flow chart illustrating a method, according to an example embodiment. The method 600 is one example of a method that may be implemented to fabricate a body-mountable device, such as one of the body-mountable device described with respect to FIGS. 1-4. For purposes of illustration, the method 600 is described below as being carried out by a fabrication device that utilizes cast or compression molding. It should be understood, however, that the method 600 may be carried out by a fabrication device that utilizes other methods for forming the polymer layers. It should also be understood that the method 600 may be carried out by more than one fabrication device.

Moreover, for purposes of illustration, the method 600 is described below in a scenario where a body-mountable device comprises an eye-mountable device. It should be understood, however, that the method 600 may involve scenarios where the body-mountable device comprises other mountable devices that are mounted on or in other portions of the human body. For example, the method 600 may involve scenarios where the body-mountable device comprises a tooth-mountable device and/or a skin-mountable device as described herein.

At block 602, the method 600 comprises molding an electronic structure to have a first curvature corresponding to a first radius of curvature. Performing block 602 may provide a molded electronic structure that is the same as or substantially similar to the molded electronic structure 530C described with respect to FIG. 5C. Similarly, performing block 602 may involve employing a molding apparatus that functions in a manner that is the same as or similar to the molding apparatus 500 described with respect to FIGS. 5A-B.

At block 604, the method 600 comprises adhering the molded electronic structure to a first polymer layer. The first polymer layer may comprise a polymer material. The fabrication device may form the polymer material to provide the first polymer layer, perhaps by compressing the polymer material using one or more molding pieces.

After the polymer material is formed into the first polymer layer, the fabrication device may cure the first polymer layer. Curing involves the hardening of a polymer material by cross-linking of polymer chains, and curing may be, for example, brought about by chemical additives, ultraviolet radiation, electron beam, and/or heat. In an example, the polymer material can be a light-curable polymer material, and the fabrication device may be configured to cure the light-curable polymer material using light, such as ultraviolet light or visible light.

The first polymer layer may be formed to have a thickness that is suitable for use in a body-mountable device. In one example, the thickness of the first polymer layer can be selected based on a particular analyte or analytes an eye-mountable device is configured to detect. For example, an optimal thickness for a first analyte may be 10 micrometers, while an optimal thickness for a second analyte may be 25 micrometers. Other examples are possible as well.

Additionally, the fabrication device may form the first polymer layer to have a second curvature. The second curvature may correspond to a second radius of curvature. In an example in which the first polymer layer is a posterior layer of an eye-mountable device, the second curvature may be substantially similar to the curvature of a user's cornea. That is, the second radius of curvature may be substantially similar to the base curve radius of a contact lens. In one example, the first curvature is approximately equal to the second curvature. In another example, the first curvature may be greater than the second curvature. In this example, the first curvature may be based on an estimated increase in the first radius of curvature over a period of time. The difference between the first radius of curvature and the second radius of curvature may be approximately equal to the estimated increase in the first radius of curvature. Moreover, the difference between the first radius of curvature and the second radius of curvature may be within a tolerance of the estimated increase in the first radius of curvature. Other examples may also be possible.

The fabrication device may apply an adhesive to the molded electronic structure and/or the first polymer layer. The applied adhesive may facilitate adhesion of the molded electronic structure to the first polymer layer. For instance, a small amount of adhesive may be applied to the first polymer layer. Additionally or alternatively, a small amount of adhesive may be applied to the molded electronic structure. The fabrication device may then position the molded electronic structure on the first polymer layer, and the adhesive may be cured such that the molded electronic structure adheres to the first polymer layer. With this arrangement, the molded electronic structure may remain adhered to the first polymer layer in a secure location during subsequent formation steps. In some embodiments, a force and/or a torque can be applied to the molded electronic structure during curing of the adhesive.

In another example, the first polymer layer may be in a partially-cured state. As such, the first polymer layer may have a tackiness that facilitates adhesion thereto. With this arrangement, the molded electronic structure may be positioned on the first polymer layer and remain adhered to the first polymer layer in a secure location during subsequent formation steps.

At block 606, the method 600 includes forming a second polymer layer over the molded electronic structure adhered to the first polymer layer. The fabrication device may form a second polymer layer over the first polymer layer and the structure, such that the molded electronic structure is fully enclosed by the first polymer layer and the second polymer layer, perhaps by using one or more molding pieces to compress the polymer material and the molded electronic structure adhered to the first polymer layer.

In some embodiments, the second polymer layer can extend between adjacent conductive loops, such as the conductive loop 572A and the conductive loop 572B and/or the conductive loop 572B and the conductive loop 572C, in the plurality of conductive loops 572. With this arrangement, the second polymer layer may bond to the first polymer layer between the adjacent conductive loops in the plurality of conductive loops 572.

After the second polymer layer is formed, the fabrication device may cure the second polymer layer. In one example, the second polymer layer can be cured like the first polymer layer. However, in other examples, the second polymer layer may be cured by different techniques than the first polymer layer. The second polymer layer can be cured by any of the techniques mentioned herein. In another example, the fabrication device may also cure the first polymer layer at this stage.

After the second polymer layer is cured, there may not be a visible boundary line separating the first polymer layer from the second polymer layer. As noted, FIG. 3A illustrates the eye-mountable device 310. In particular, FIG. 3A illustrates the eye-mountable device 300 includes the transparent polymer 320. The transparent polymer 320 can be arranged like the first polymer layer and the second polymer layer.

The fabrication device may be configured to form the second polymer layer to have a thickness suitable for a body-mountable device. In one example, the fabrication device may form the second polymer to have a defined a thickness of the second polymer layer. In another example, the fabrication device may be configured to define a final thickness of a body-mountable device, such as the eye-mountable device 310. Further, the fabrication device may be configured to allow for a layer having a given desired thickness between the first and second polymer layers (in addition to a thickness of the first polymer).

In one example, the second polymer layer may have a thickness of greater than 50 micrometers. However, in other examples, the second polymer layer can have a thickness between 50 and 300 micrometers, such as 130 micrometers. It should be understood that since the second polymer layer molds over the molded electronic structure, the second polymer layer may not have a uniform thickness. For instance, the thickness of the second polymer layer above an electronic component of the molded electronic structure may be less than the thickness of the second polymer layer is not touching the electronic component.

In another example, the thickness of the second polymer layer may depend on a particular analyte or analytes that the body-mountable device, such as the eye-mountable device 310, is configured to detect. For example, an optimal thickness for a first analyte may be 10 micrometers, while an optimal thickness for a second analyte may be 25 micrometers. Other examples are possible as well.

The second polymer layer may be composed of the same polymer material as the first polymer layer. However, in other examples, the second polymer layer may be composed of a different polymer material than the first polymer layer. The second polymer layer can be any one of the polymer materials mentioned herein. In an example, the structure can be more rigid than the second polymer layer.

The second polymer layer may define an anterior side of an eye-mountable device. That is, the second polymer layer defines an outer edge of the eye-mountable device. When mounted on an eye of a user, the anterior side of the eye-mountable device defined by the second polymer layer corresponds to the side of the device that is not touching the eye of the user. The curvature of the second polymer layer may depend on a different characteristic of a contact lens prescription, such as a magnification power of a contact lens.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

We claim:

1. An eye-mountable device comprising:
   a first polymer layer;
   an electronic structure adhered to the first polymer layer, wherein the electronic structure comprises a rigid bio-compatible polymer, an antenna, a sensor, and an electronic device, wherein the electronic structure includes at least one slit, and wherein the electronic structure is molded to have a first curvature; and
   a second polymer layer that is formed over the molded electronic structure adhered to the first polymer layer, wherein the molded electronic structure is more rigid than the second polymer layer, and wherein the second polymer layer bonds to the first polymer layer through the at least one slit.

2. The eye-mountable device of claim 1, wherein the first polymer layer has a second curvature, and wherein first curvature of the molded electronic structure is approximately equal to the second curvature of the first polymer layer.

3. The eye-mountable device of claim 1, wherein the first polymer layer has a second curvature, and wherein the first curvature of the molded electronic structure is less than the second curvature of the first polymer layer.

4. The eye-mountable device of claim 3, wherein a difference between the first curvature and the second curvature is within a predetermined tolerance.

5. The eye-mountable device of claim 1, wherein the molded electronic structure includes at least one support structure that limits a change in the first curvature over a period of time, wherein the at least one slit comprises a plurality of slits, and wherein the at least one support structure includes a particular support structure positioned between a first slit of the plurality of slits and a second slit of the plurality of slits.

6. The eye-mountable device of claim 5, wherein the particular support structure is positioned substantially opposite the electronic device.

7. The eye-mountable device of claim 5, wherein the at least one support structure includes two support structures positioned approximately 180° apart.

8. The eye-mountable device of claim 1, wherein the at least one antenna comprises two or more conductive loops, and wherein the at least one slit provides spacing between at least two of the two or more conductive loops.

9. The eye-mountable device of claim 1, wherein the electronic structure is molded to have the first curvature by a process comprising heating the electronic structure to a predetermined temperature that is greater than a glass transition temperature of the bio-compatible polymer and less than a melting temperature of the bio-compatible polymer.

10. The eye-mountable device of claim 1, wherein the electronic structure is molded to have the first curvature after being fabricated on a substantially flat surface.

11. The eye-mountable device of claim 10, wherein the electronic structure is molded to have the first curvature by a process that reduces a tendency of the electronic structure to flatten over time.

12. The eye-mountable device of claim 1, wherein the electronic structure is molded to have the first curvature prior to being adhered to the first polymer layer.

13. The eye-mountable device of claim 1, wherein the rigid bio-compatible polymer is polyethylene terephthalate or dichlorodi-p-xylylene.

14. The eye-mountable device of claim 1, wherein the first polymer layer and second polymer layer each comprise a non-rigid polymeric material.

15. The eye-mountable device of claim 1, wherein the first polymer layer defines a posterior side of the eye-mountable device and the second polymer layer defines an anterior side of the eye-mountable device.

16. The eye-mountable device of claim 8, wherein the spacing between the at least two conductive loops is between 100 micrometers and 200 micrometers.

* * * * *